United States Patent
Rahmes et al.

(10) Patent No.: US 10,631,799 B2
(45) Date of Patent: Apr. 28, 2020

(54) DENTAL IMAGE COLLECTION DEVICE PROVIDING OPTICAL ALIGNMENT FEATURES AND RELATED SYSTEM AND METHODS

(71) Applicant: HARRIS CORPORATION, Melbourne, FL (US)

(72) Inventors: Mark D. Rahmes, Melbourne, FL (US); Marc Waterloo, Watchung, NJ (US); Mervin D. Fagan, San Antonio, TX (US); Lawrence W. Shacklette, Melbourne, FL (US)

(73) Assignee: HARRIS CORPORATION, Melbourne, FL (US)

( * ) Notice: Subject to any disclaimer, the term of this patent is extended or adjusted under 35 U.S.C. 154(b) by 407 days.

(21) Appl. No.: 15/371,539

(22) Filed: Dec. 7, 2016

(65) Prior Publication Data

US 2018/0153485 A1      Jun. 7, 2018

(51) Int. Cl.
| | | |
|---|---|---|
| A61B 6/14 | (2006.01) | |
| A61B 6/00 | (2006.01) | |
| A61B 6/08 | (2006.01) | |
| A61C 5/90 | (2017.01) | |
| G03B 42/04 | (2006.01) | |

(52) U.S. Cl.
CPC .............. *A61B 6/145* (2013.01); *A61B 6/08* (2013.01); *A61B 6/5235* (2013.01); *A61B 6/5241* (2013.01); *A61B 6/587* (2013.01); *A61C 5/90* (2017.02); *G03B 42/042* (2013.01)

(58) Field of Classification Search
CPC ........... A61B 6/145; A61B 6/587; A61B 6/08; A61B 6/5235; A61C 5/90; G03B 42/042
See application file for complete search history.

(56) References Cited

U.S. PATENT DOCUMENTS 5,828,722 A * 10/1998 Ploetz ...................... A61B 6/08
                                                                378/38
6,078,699 A *  6/2000 Lobregt ................ A61B 6/481
                                                                348/E5.086

(Continued)

FOREIGN PATENT DOCUMENTS

WO        2004017833        3/2004

OTHER PUBLICATIONS

Dental Scintillators—CsI coated fibre optic plates optimised for dental applications: www. scintacor.com; tech.csi-dental 001/Mar. 2005; pp. 2.

(Continued)

*Primary Examiner* — David J Makiya
*Assistant Examiner* — Soorena Kefayati
(74) *Attorney, Agent, or Firm* — Allen, Dyer, Doppelt + Gilchrist, P.A.

(57) ABSTRACT

A dental imaging system may include an X-ray source, a first optical alignment device, and a dental image collection device. The dental image collection device may include a mouthpiece, at least one electronic X-ray sensor carried by the mouthpiece, and a second optical alignment device carried by the mouthpiece and cooperating with the first optical alignment device to facilitate optically aligning the mouthpiece with the X-ray source. The system may also include a dental image processing device coupled to the at least one electronic X-ray sensor.

14 Claims, 10 Drawing Sheets

(56) References Cited

U.S. PATENT DOCUMENTS

| | | | | |
|---|---|---|---|---|
| 6,381,302 | B1* | 4/2002 | Berestov | A61B 6/022 378/41 |
| 6,592,371 | B2* | 7/2003 | Durbin | A61C 9/0053 433/214 |
| 7,336,763 | B2* | 2/2008 | Spartiotis | A61B 6/14 378/40 |
| 7,630,797 | B2* | 12/2009 | Garceau | G08G 5/0021 345/582 |
| 8,002,465 | B2 | 8/2011 | Ahn | |
| 8,331,528 | B2* | 12/2012 | Kayzerman | H04N 5/3415 378/38 |
| 8,750,590 | B2* | 6/2014 | Greenberg | A61B 6/14 382/131 |
| 9,433,387 | B2 | 9/2016 | Ahn | |
| 2007/0081631 | A1* | 4/2007 | Kay | A61B 6/14 378/168 |
| 2007/0162193 | A1 | 7/2007 | Garceau et al. | |
| 2008/0080758 | A1* | 4/2008 | Hoppe | A61B 6/583 382/132 |
| 2008/0089468 | A1* | 4/2008 | Heigl | A61B 6/032 378/20 |
| 2010/0279248 | A1* | 11/2010 | Mourad | A61B 5/0534 433/29 |
| 2012/0171634 | A1* | 7/2012 | Graham | A61B 6/145 433/29 |
| 2012/0307965 | A1* | 12/2012 | Bothorel | A61B 6/14 378/10 |
| 2012/0313943 | A1* | 12/2012 | Tsukagoshi | A61B 5/055 345/424 |
| 2013/0030285 | A1* | 1/2013 | Vaillant | A61B 6/12 600/424 |
| 2013/0181978 | A1* | 7/2013 | Tsukagoshi | A61B 6/466 345/419 |
| 2013/0260340 | A1* | 10/2013 | Stegall | A61B 6/145 433/217.1 |
| 2014/0126687 | A1* | 5/2014 | Yoshikawa | A61B 6/145 378/16 |
| 2014/0342301 | A1* | 11/2014 | Fleer | G06T 15/08 433/27 |
| 2015/0320320 | A1* | 11/2015 | Kopelman | A61B 5/4547 433/24 |
| 2015/0359504 | A1* | 12/2015 | Zhou | A61B 6/547 378/38 |
| 2016/0014396 | A1 | 1/2016 | Glinec et al. | |
| 2016/0220212 | A1* | 8/2016 | Duewer | A61B 6/027 |
| 2016/0287198 | A1* | 10/2016 | Abramovich | A61B 6/105 |
| 2017/0143445 | A1* | 5/2017 | Abkai | A61B 90/39 |
| 2017/0281110 | A1* | 10/2017 | Mandelkern | A61B 6/025 |
| 2017/0332986 | A1* | 11/2017 | Grondin | A61B 6/588 |
| 2018/0070896 | A1* | 3/2018 | Kim | A61B 6/08 |
| 2018/0160932 | A1* | 6/2018 | Abkai | A61B 5/7278 |

OTHER PUBLICATIONS

Dentalaire DTX—Dental Imaging System: www.dentalaireroducts. com; retreived from Internet Sep. 27, 2016; pp. 2.

Rahmes et al. "Dental non-linear image registration and collection method with 3d reconstruction and change detection" SPIE Medical Imaging Conference 10132; Physics of Medical Imaging—Session PS12: Posters: Radiography: X-Ray Imaging, Fluoroscopy, and Tomosynthesis: Feb. 15, 2017; pp. 8.

Godard et al. "Unsupervised Monocular Depth Estimation with Left-Right Consistency" http://visual.cs.ucl.ac.uk/pubs/monoDepth: retrieved from Internet Nov. 8, 2016: pp. 8.

Evangelidis et al. "Parametric Image Alignment using Enhanced Correlation Coefficient Maximization", IEEE Trans. on PAMI, vol. 30, No. 10, 2008. pp. 8.

Kelly et al. "Automated Sea Floor Extraction from Underwater Video", SPIE, From Conference vol. 9827; Ocean Sensing and Monitoring VIII; Apr. 17, 2016; Abstract Only.

Rahmes et al. "Production System for Autonomous 3-Dimensional Modeling with LiDAR, IFSAR, and Photogrammetric DSM Data", www.asprs.org/wp-content/uploads/2011/01/0060.pdf ASPRS 2007 Annual Conference Tampa, Florida # May 7-11, 2007; pp. 9.

Vincent et al. "Detecting planar homographies in an image pair" InProceedings of the 2nd International Symposium on Image and Signal Processing and Analysis Jun. 2001 (pp. 182-187). www.eiti.uottawa.ca/school/research/viva/papers/homographie.pdf: pp. 8.

Brubaker et al. 2503 Tutorial; 2D Homographies, 2004-2008, www.sci.utah.edu/~gerig/CS6640-F2010/tutorial2-homographies.pdf pp. 15.

Williamson "Digital radiography in dentistry: Moving from film-based to digital imaging" American Dental Assistants Association, Chicago, media.dentalcare.com/media/en-US/education/ce350/ce350.pdf, retrieved from internet Nov. 8, 2016; gs. 23.

http://www.buyamag.com/graphics/dental_education_posters_14.jpg; May 9, 2016.

* cited by examiner

DENTAL IMAGE COLLECTION DEVICE PROVIDING OPTICAL ALIGNMENT FEATURES AND RELATED SYSTEM AND METHODS

TECHNICAL FIELD

The present disclosure relates to medical devices and, more particularly, to medical devices for use with diagnostic imaging and related methods.

BACKGROUND

Diagnostic imaging, such as with computerized tomography (CT) scan, magnetic resonance imaging (MRI) scans, and X-rays, are important tools in the diagnosis and treatment of medical conditions in patients. Such imaging not only allows medical practitioners to locate diseased or problem areas inside of a patient, but also to track the progression of such areas over time. Accordingly, the ability to properly position patients is important for consistent and accurate imaging results so that meaningful comparisons can be made between different images.

U.S. Pat. No. 8,002,465 to Ahn discloses a system for ensuring that a patient is positioned correctly during radiation therapy and diagnostic imaging. The system helps ensure that a patient is positioned correctly, e.g., identically with an original planning scan if the patient is to undergo radiotherapy. The system also detects if there is patient movement during a scan. The patient is immobilized based on a specific site of interest by using positioning sensors that record patient physical orientation based on measurements of patient weight distribution and pressure distribution.

With respect to dentistry, many dental lesions and conditions may only be detected through the use of dental radiographs (X-rays). For example, without the use of a dental radiograph, doctors cannot see directly between teeth or under gums. In many instances, despite significant underlying pathology, the patient may present with no signs or symptoms of disease. Yet, without the use of dental radiographs, the dentist would be limited to detecting disease only when it was visible in the mouth. Dental x-rays enable the detection of disease much more reliably and sooner than a clinical examination alone. This allows the dental practitioner to identify and resolve problems early, with the patient potentially avoiding extensive pain and costly treatments.

By way of example, X-rays may be used for numerous purposes in dentistry, including to: identify decay beneath an existing filling; reveal bone loss associated with gum disease; reveal changes in bone or a root canal caused by infection; facilitate the preparation for tooth implants; determine whether the space in the mouth is sufficient to accommodate a child's incoming teeth; check for development of wisdom teeth; and reveal other abnormalities. However, typical dental X-ray devices allow for a large difference in perspective, making it difficult to analyze dental change over time.

SUMMARY

A dental imaging system may include an X-ray source, a first optical alignment device, and a dental image collection device. The dental image collection device may include a mouthpiece, at least one electronic X-ray sensor carried by the mouthpiece, and a second optical alignment device carried by the mouthpiece and cooperating with the first optical alignment device to facilitate optically aligning the mouthpiece with the X-ray source. The system may also include a dental image processing device coupled to the at least one electronic X-ray sensor.

More particularly, the first optical alignment device may comprise an optical target, and the second optical alignment device may comprise at least one optical source. In accordance with another example, the first optical alignment device may comprise at least one optical detector. In accordance with one embodiment, the first optical alignment device may be carried by the X-ray source. By way of example, the second optical alignment device may comprise a plurality of laser light sources. In accordance with another example, the second optical alignment device may comprise a laser light source and an optical element associated therewith.

Furthermore, the at least one X-ray sensor may comprise a plurality of integrated circuit (IC) sensors. In addition, the image processing device may be configured to generate a composite image for a given patient from dental images collected at different times. By way of example, the composite image may comprise a disparity map image. Moreover, the dental image processing device may be configured to process dental images using a homography algorithm prior to generating the composite image, for example. In accordance with one example embodiment, the system may further include at least one actuator coupled to the X-ray source, and the dental image processing device may be configured to operate the at least one actuator based upon the first and second optical alignment devices.

A related dental imaging collection device, such as the one described briefly above, and method for making such a dental imaging collection device, are also provided. A method for collecting dental imagery is also provided which may include inserting a dental image collection device in a patient's mouth including a mouthpiece, at least one electronic X-ray sensor carried by the mouthpiece, and a second optical alignment device carried by the mouthpiece. The dental image collection device may be coupled to a dental image processing device. The method may further include aligning an X-ray source with the mouthpiece by optically aligning a first optical alignment device and the second optical alignment device, and using the X-ray source and a dental image processing device to collect X-ray data from the electronic X-ray sensor.

DETAILED DESCRIPTION OF THE EMBODIMENTS

The present description is made with reference to the accompanying drawings, in which exemplary embodiments are shown. However, many different embodiments may be used, and thus the description should not be construed as limited to the particular embodiments set forth herein. Rather, these embodiments are provided so that this disclosure will be thorough and complete. Like numbers refer to like elements throughout, and prime and multiple prime notation are used to indicate similar elements in different embodiments.

Figure 1:
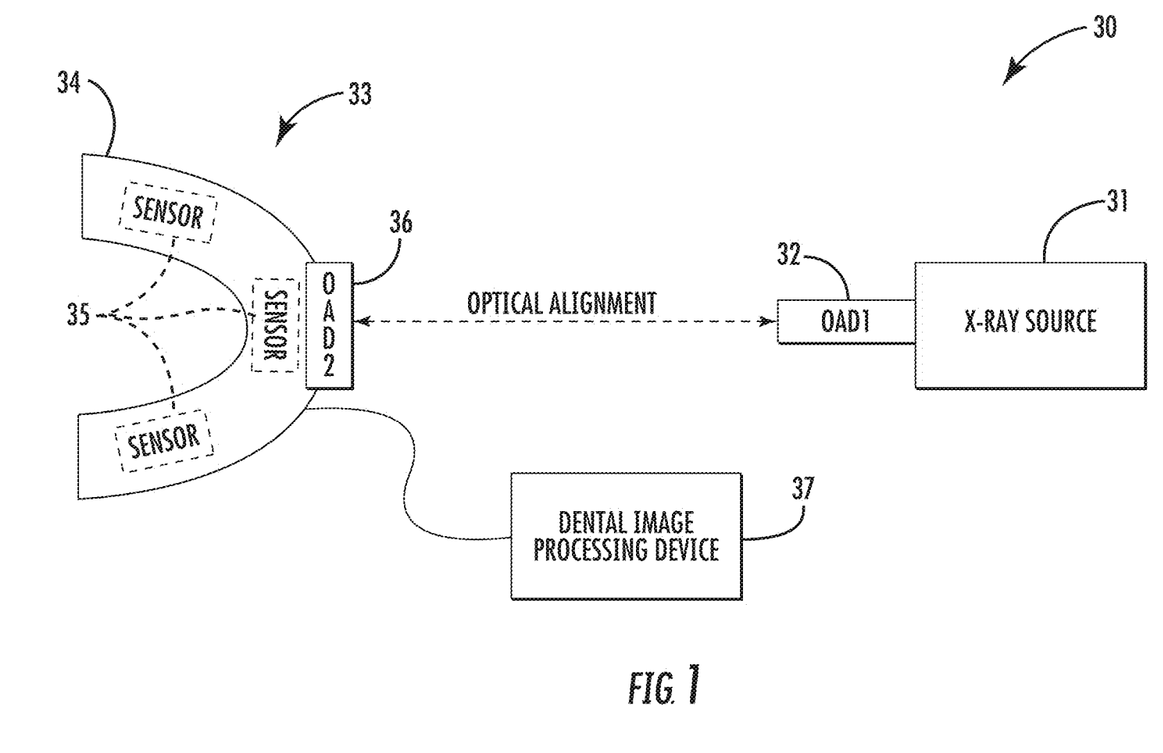
FIG. 1 is a schematic block diagram of a dental imaging system in accordance with an example embodiment.
Figure 2:
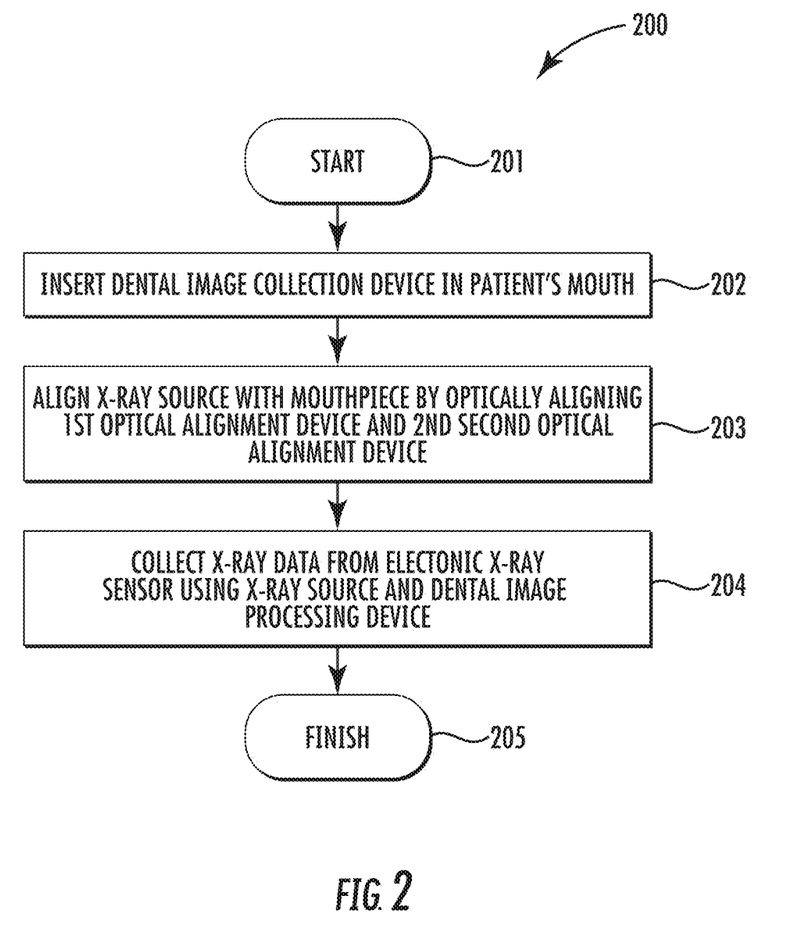
FIG. 2 is a flow diagram illustrating method aspects associated with the system of FIG. 1.

Referring initially to FIG. 1 and the flow diagram 200 of FIG. 2, a dental imaging system 30 and associated method of using the system are first described. The system 30 illustratively includes an X-ray source 31, a first optical alignment device 32, and one or more dental image collection devices 33. More particularly, the dental image collection device 33 illustratively includes a mouthpiece or dental tray 34, one or more electronic X-ray sensors 35 carried by the mouthpiece, and a second optical alignment device 36 carried by the mouthpiece. Beginning at Block 201, after the mouthpiece 34 is inserted in a patient's mouth, at Block 202, the second optical alignment device 36 cooperates with the first optical alignment device 32 to facilitate optically aligning the mouthpiece with the X-ray source, at Block 203. The system 30 also illustratively includes a dental image processing device 37 coupled to the electronic X-ray sensor(s) 35 to collect X-ray data therefrom responsive to the X-ray source 31, at Block 204, which illustratively concludes the method of FIG. 2 (Block 205). As images are captured, they may be saved in a memory which may be part of the dental image processing device or remotely located (e.g., on a network or cloud server).

Figure 3:
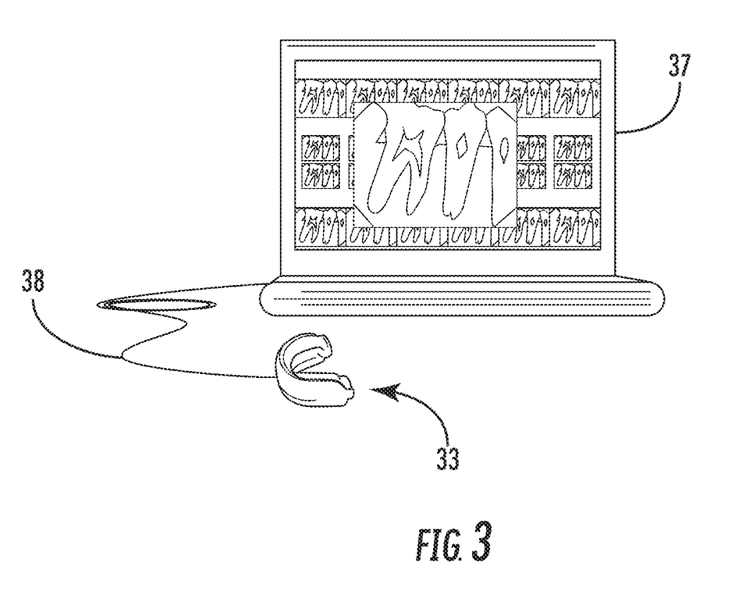
FIG. 3 is an example implementation of the dental image collection and processing devices of the system of FIG. 1.

In the example illustrated in FIG. 3, the dental image processing device 37 is a laptop computer, but other suitable computing devices may be used in different embodiments, such as desktop computers, tablet computers, etc. Moreover, in the illustrated example, the electronic X-ray sensors 35 may be coupled to the dental image processing device via a wired connection 38, such as a universal serial bus (USB) cable (e.g., a standard or micro-USB cable) or other suitable communications link. In this regard, a USB transceiver (not shown) may be incorporated within the mouthpiece 34 to not only provide power to the sensors 35 and the optical alignment device 36, but also to control digital data communication between the sensors and the dental image processing device 37.

Figure 4:
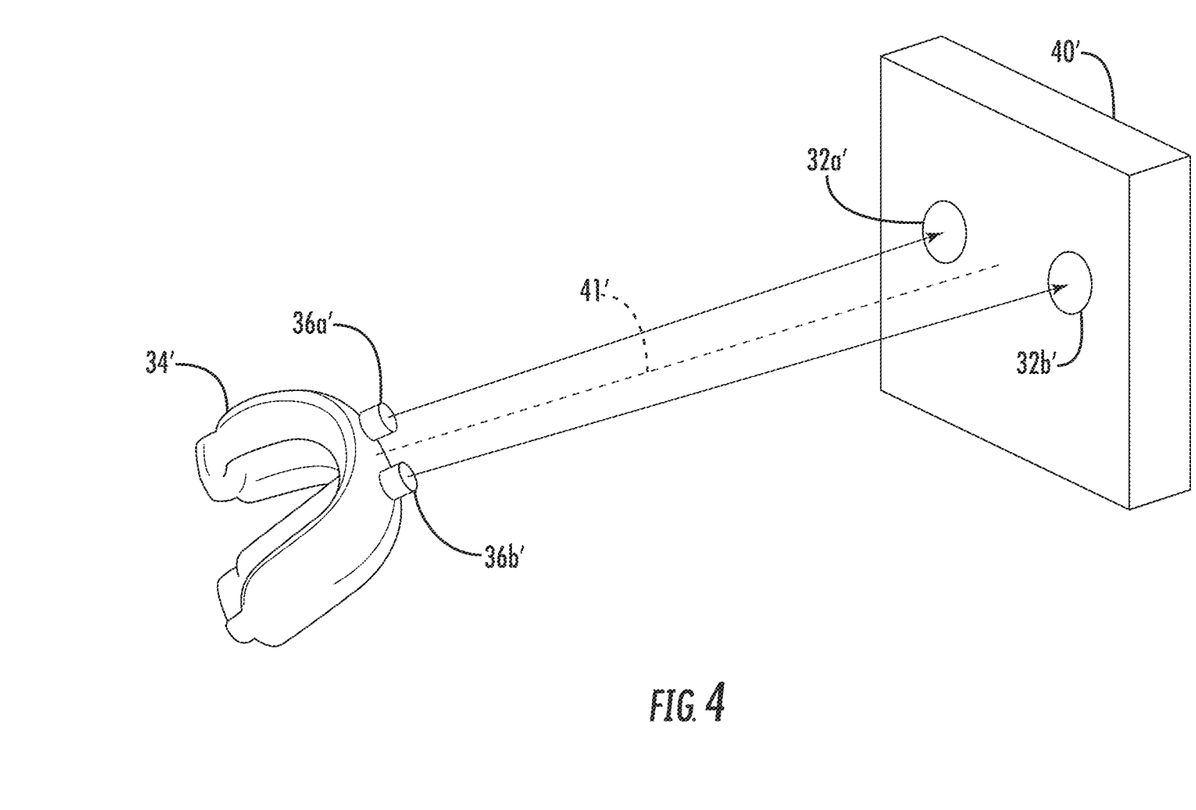
FIGS. 4 and 5 are perspective views of different optical alignment device configurations which may be used with the system of FIG. 1.

More particularly, in accordance with one example embodiment illustrated in FIG. 4, the first optical alignment device comprises a pair of optical targets 32a' and 32b', which in the illustrated example are circles on a substrate 40' (e.g., a housing of the X-ray source), and the second optical alignment device comprises a pair of corresponding optical sources 36a', 36b', such a laser lights, for example. More particularly, each of the optical sources 36a', 36b' may be oriented at respective angles from boresight 41' to the substrate 40' on which the optical targets 32a', 32b' are located, so that when the mouthpiece 34' and the X-ray source are in the correct alignment, the light spots (e.g., laser light spots) from the optical sources are centered or aligned on or within the optical targets.

It will be appreciated that other shapes and configurations of optical targets may be used in different embodiments, but in the illustrated configuration centering of the light spots within the two targets 32a', 32b' helps provide for roll alignment. Moreover, when circular light spots are used, if the shape of the spot matches the shape of the target, this confirms that the relative pitch between the mouthpiece 34' and the X-ray source is correct (too much or little pitch will make the light spot ovular rather than circular, for example). Moreover, the size of the light spot relative to the size of the target circle may also be used to provide an indication of a prescribed distance between the mouthpiece 34' and the optical targets 32a', 32b'. That is, when the size of the light spot is the same size as the target circles, then the mouthpiece 34' and the optical targets 32a', 32b' will be at a set distance. As such, since the pitch, roll, and distance may relatively easily be made consistent by different dental technicians, all of the images taken by the system may advantageously be from substantially the same perspective to allow for much more accurate comparisons over time.

It should be noted that in some embodiments the substrate 40' may be something other than the housing of the X-ray source. For example, the substrate 40' may be a target board that is spaced apart a given distance from the X-ray source. For example, the substrate 40' may be carried by a radial arm (not shown) at a predetermined angle to boresight 41' (e.g., 45°, 90°, etc.), allowing the X-ray source to be aligned at a predetermined angle to the side of a patient's mouth to take bite wing X-rays from a consistent position. That is, the configurations set forth herein advantageously allow for X-ray images to be taken from numerous different perspectives, yet at consistent orientations which may be relatively easily compared with one another over time.

Figure 5:
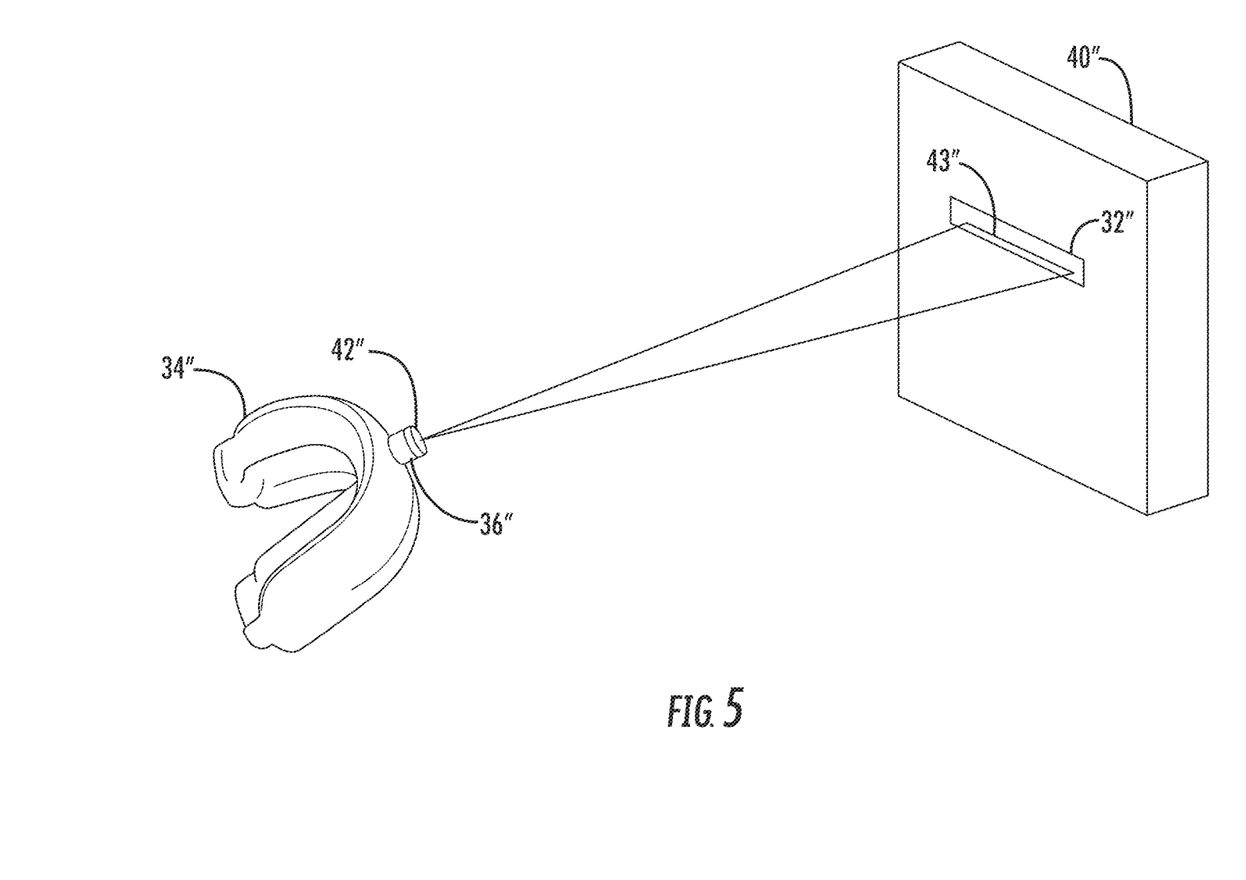

Another example optical alignment configuration is shown in FIG. 5. Here, the first optical alignment device is an optical detector 32" (e.g., a CCD, etc.) carried on the substrate 40", and the second optical alignment device illustratively includes a laser light source 36" and an optical element 42" associated therewith. More particularly, the optical element 42" may be a diffractive optical element (DOE) to shape the laser light beam into a desired shape, which in the illustrated example is a straight line 43", although other shapes or patterns may also be used in different embodiments. Here, the straight line pattern 43" on the area of the optical detector 32" may not only again confirm that the pitch and roll of the laser beam is correct, but also that the mouthpiece 34" is at the desired distance away from the optical detector 32", and thus the X-ray source. That is, the width of the line indicates the distance between the mouthpiece 34" and the optical detector 32", as will be appreciated by those skilled in the art. Thus, the X-ray source and/or the patient may be moved until the optical detector confirms that the laser light line 43" is aligned appropriate with the optical detector 32" as shown. In some embodiments, optical targets or detectors may be recessed within the substrate (or have raised surface features around them) so that light from the optical source(s) only strikes the target/detector when it comes from the desired angle, for example.

In the example illustrated in FIG. 1, three integrated circuit (IC) X-ray sensors 35 are spaced apart along the mouthpiece 34, although different numbers of sensors may be used in different embodiments. By way of example, the X-ray sensor 35 may include a digital CsI scintillator which captures x-rays and converts them to visible light, as will be appreciated by those skilled in the art. More particularly, the sensors 35 may include needle crystals that guide light toward a sensor array. Fiber optic faceplates enable dentists to view near-instant, high-resolution images, while greatly reducing sensor exposure to harmful X-rays. In cephalometric, panoramic, and intraoral digital X-ray systems, faceplates provide an X-ray barrier between the X-ray emitter and the semiconductor device (CCD or CMOS). This barrier prolongs sensor life, reduces background noise, and improves image quality. The X-ray sensors 35 may be sized so that two or more sensors fit along the length of the mouthpiece 34 to provide enhanced sensor accuracy if desired, although in some embodiments a single sensor may be used. In another example embodiment, a continuous sensor array may be formed along the length of the mouthpiece 34.

As electronic sensors are much more sensitive to X-rays than film, the system 30 may advantageously allow a lower radiation dosage to be used than with standard X-ray films. In addition to the lower X-ray dosage exposure to patients and standardized collection images achieved by the system 30, the system may accordingly also help to reduce dentist visit times, generate higher quality images, facilitate the transfer of dental records, and be environmentally friendly. Moreover, the dental image collection devices 33 may help standardize perspective X-ray collection and make it easy to register and analyze change in collections over time. The mouthpiece 34 may be fitted to a person like a sports mouth guard, with several available sizes, and be cleaned in the same manner as other dental tools. The dental image collection device 33 may be formed by first molding the mouthpiece 34, and then attaching the sensor(s) 35 and second optical alignment device(s) 36 thereto. In other embodiments, the sensor(s) 35 and second optical alignment device(s) 36 may first be placed in a mold, and then the mouthpiece material poured into the mold to form the mouthpiece 34 with these components embedded therein. Moreover, a communications port (USB) and other circuitry may also be similarly incorporated during the manufacturing process, as noted above.

As such, the dental image collection device 33 provides for an enhanced dental imaging methodology which is simplified by placing the mouthpiece 34, with miniaturized digital electronics, in the patient's mouth. In some embodiments where enhanced accuracy is desired, after an initial X-ray is taken, it may then be compared to a standard. From the comparison, a determination is made as to whether the collection angle and scale are sufficiently similar to the ideal position of average teeth (if this is the first collection), or to the patient's previous dental X-ray image. That is, the dental image collection device 33 advantageously allows for standardized pose correction angles and distance via algorithms for current dental images with respect to an ideal teeth model or a prior image of the patient's teeth. An example dental image comparison approach is discussed further below.

Figure 6:
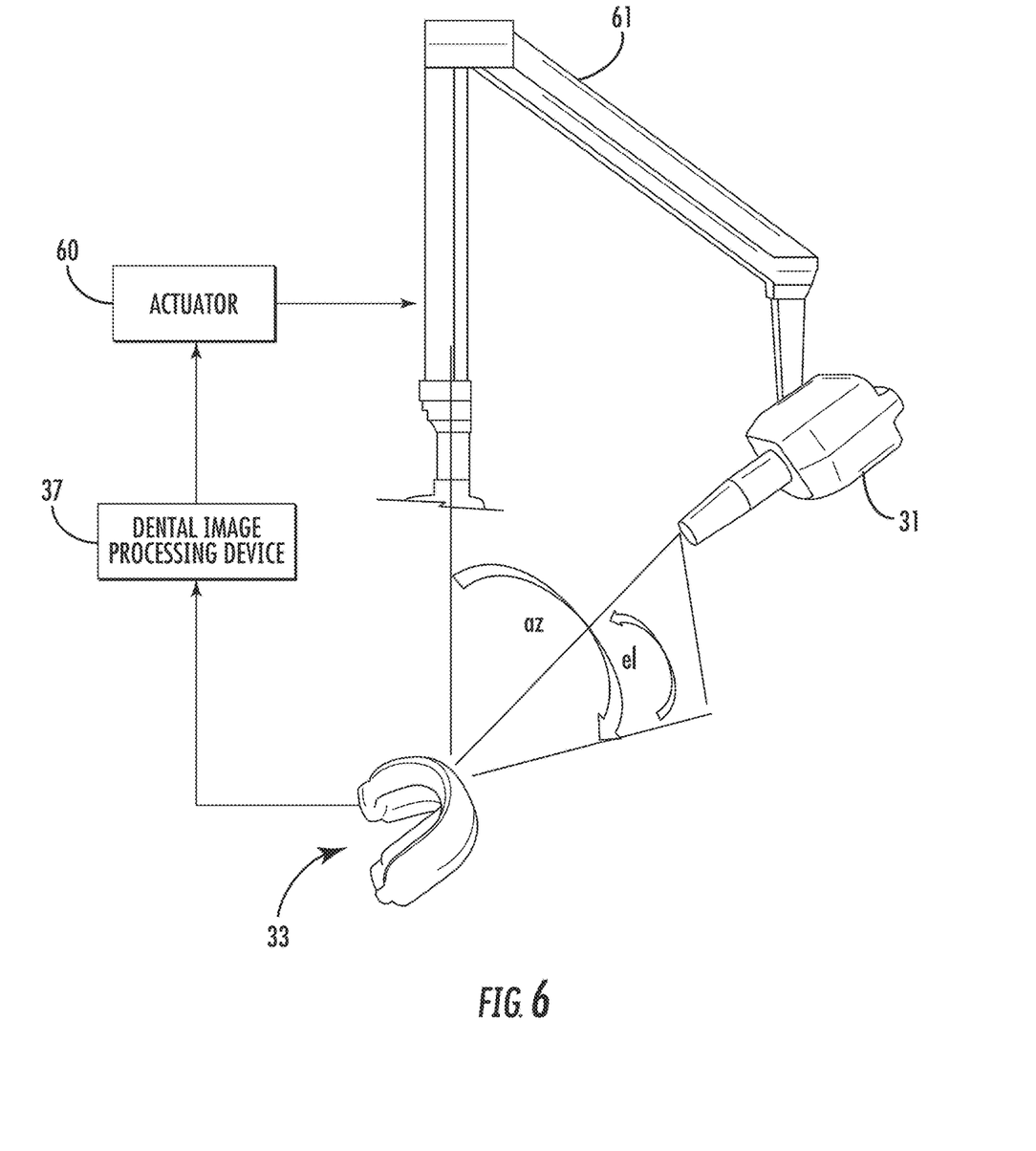
FIG. 6 is a schematic view illustrating an automated X-ray source positioning configuration which may be used with the system of FIG. 1.

Turning to FIG. 6, in some embodiments the positioning of the X-ray source 31 may be robotic and automated. In the illustrated example, the system 30 further illustratively includes one or more actuators 60 which may be controlled by the dental image processing device 37 based upon feedback from the first optical alignment device 32 and/or second optical alignment device 36. As noted above, the actuator(s) 60 may move the X-ray source 31 to different locations via an arm 61 to make multiple exposures from different beam angles, represented as azimuth (az) and elevation (el) in FIG. 6. In accordance with one example embodiment, the first and second optical alignment devices 32, 36 may be aligned in a forward or head-on position, and then while the patient remains still the actuator(s) 60 moves the X-ray source 31 around the patient's head to the other standardized imaging locations.

In addition to providing for consistent dental image collection, the dental image processing device 37 may also be used for enhanced dental image comparison of dental images whether the images are taken from a consistent perspective or not. In accordance with one example embodiment, an Enhanced Correlation Coefficient (ECC) algorithm may be used, which is a direct (gradient-based) image registration algorithm. Based on gradient information, it achieves high accuracy in parameter estimation (i.e., sub-pixel accuracy). Its performance is invariant to global illumination changes in images since it considers correlation coefficient (zero-mean normalized cross correlation) as an objective function. The algorithm takes as input two unregistered images (i.e., input image and template image) and estimates a 2D geometric transformation that, applied to the input image, generates a warped image registered to the template image. In one example embodiment, a pyramid-based framework may be used that compensates for large displacements.

Figure 7:
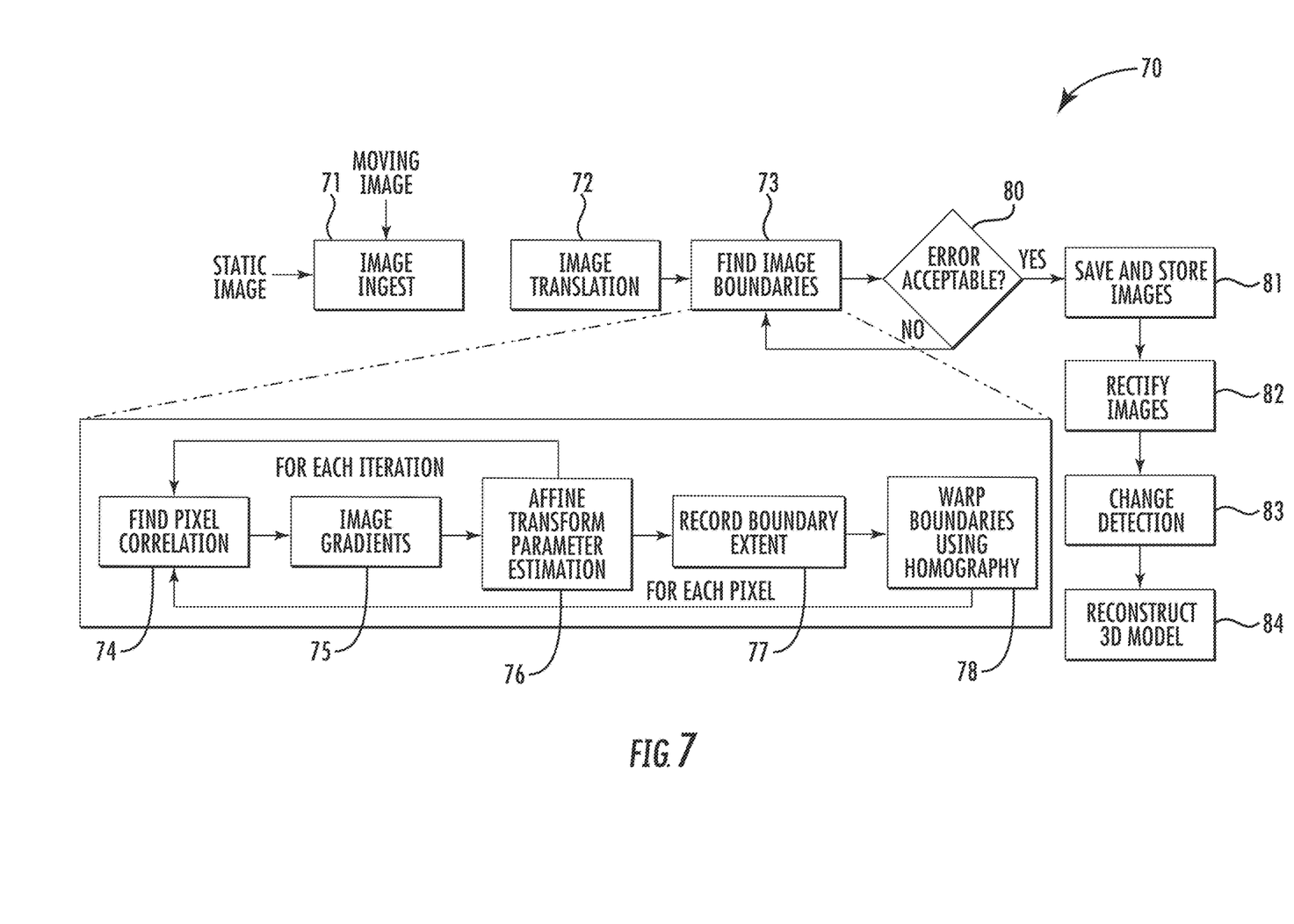
FIG. 7 is a flow diagram illustrating additional method aspects in accordance with an example embodiment.

Referring additionally to the flow diagram 70 of FIG. 7, an example image registration and change detection/comparison process is now described. Generally speaking, moving and static images are ingested, at Block 71, followed by image translation and image boundary location, at Blocks 72-73. The moving and static images may correspond to previously captured and currently captured dental images for a given patient using the dental image collection device 33 described above, for example. However, in some embodiments, the comparison techniques described herein may be used against images which were not captured using the dental image collection device 33. For example, dental images from service records, etc., may be compared to images taken from dental remains for identification purposes. In such cases, the previously stored images may be stored in a database with those of many different people, and the comparison may be made across the database, and not just against images for a known patient.

The boundary location may include finding pixel correlation, at Block 74, calculating image gradients, at Block 75, performing affine transformation parameter estimation, at Block 76, recording boundary extent, at Block 77, and warping the boundaries using homography, at Block 78, as will be described further below. If an error between the ingested images is acceptable (i.e., below an error threshold), at Block 80, then the images may be stored and rectified, at Blocks 81-82, and processed to determine a change detection therebetween (e.g., via a composite image such as disparity map), followed by reconstruction of a 3D model showing the changes, at Blocks 83-84. If the error is not acceptable, then the steps illustrated at Blocks 74-78 may be repeated.

Overlapping data enables derivation of depth or height information for 3D teeth reconstruction. A disparity map may be created using parallax from overlapping viewpoints of a given area and relative height data to optionally create a textured 3D map. The overlapping data may be used to determine the depth of features in the mouth. With multiple view angles of the same features from overlapping areas, feature parallax may advantageously be used to extract 3D data. The image parallax may be converted into a disparity map, within which height data is assigned to each image pixel. Higher feature parallax in successive frames indicates greater depth. 3D reconstructed data may be produced using adaptive noise removal, a 2D median filter, and 2D order statistic filtering, for example.

Figure 8:
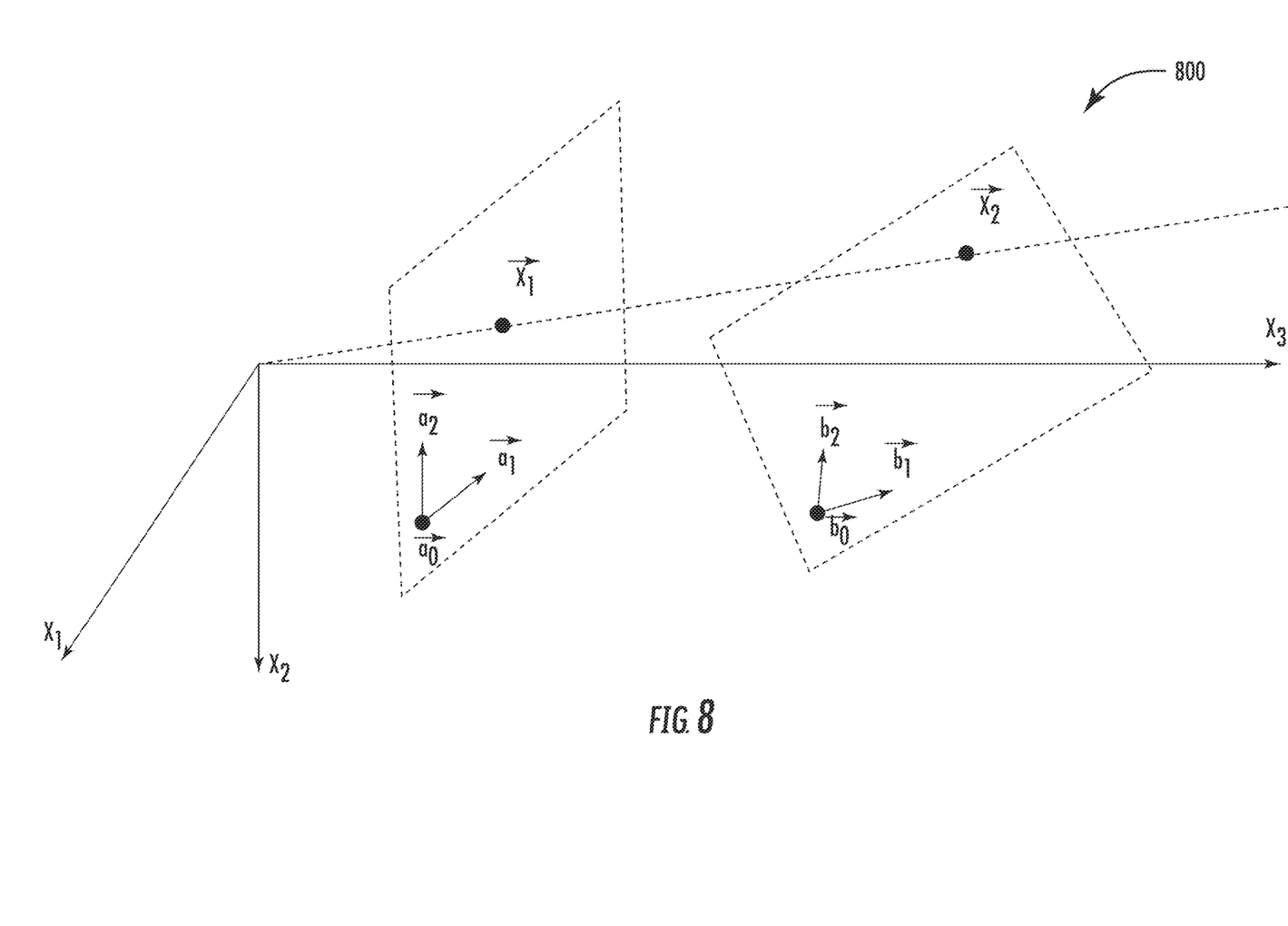
FIG. 8 is a schematic diagram illustrating a homography image processing approach which may be used in the method of FIG. 7.
Figure 9:
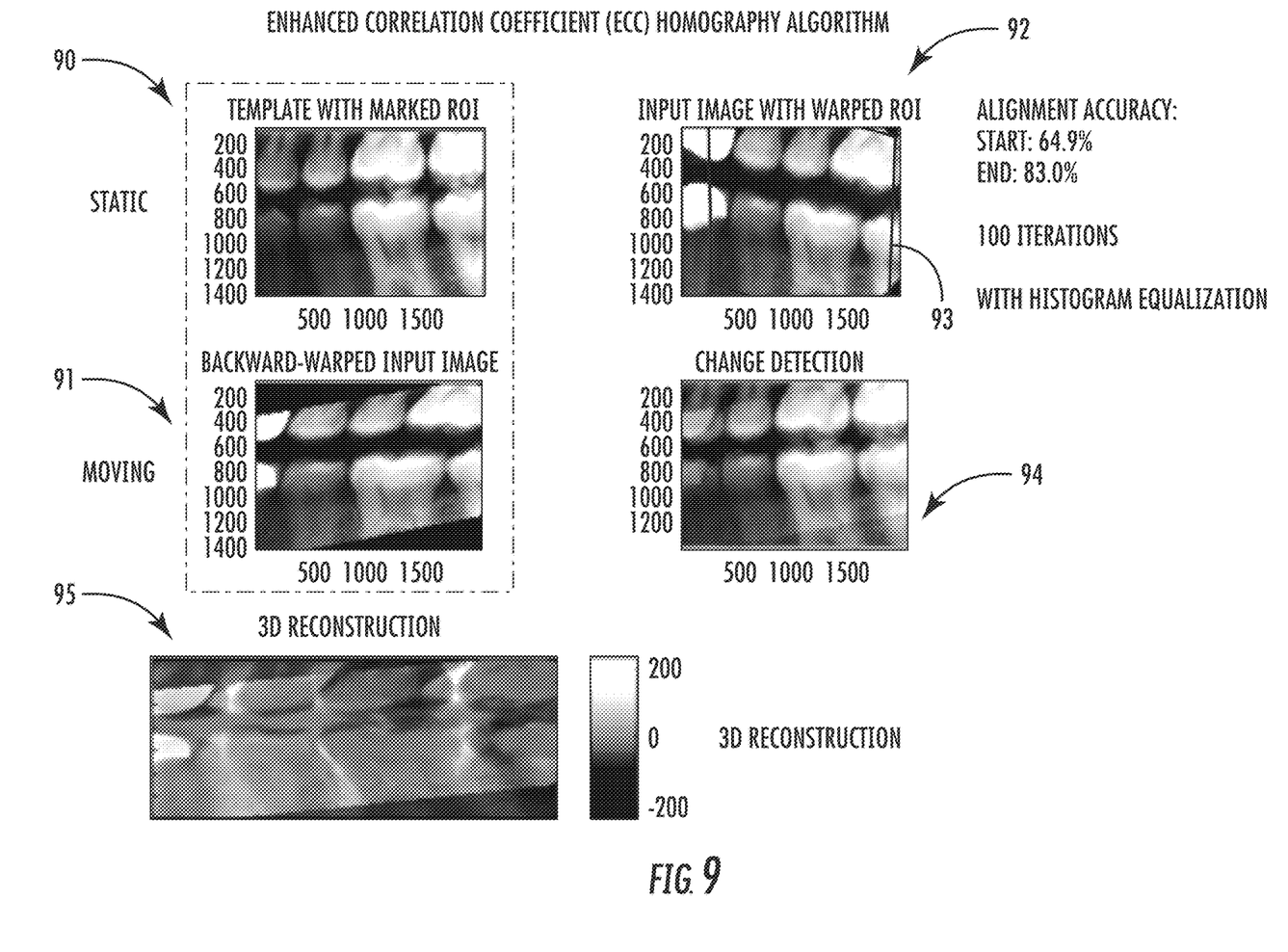
FIG. 9 is a series of dental X-rays illustrating composite dental image generation in accordance with an example embodiment.
Figure 10A:
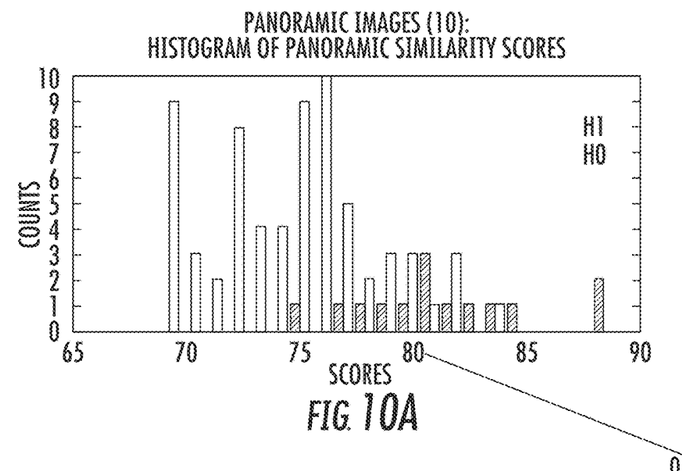
FIGS. 10(a)-(c) are a series of histograms.
Figure 10B:
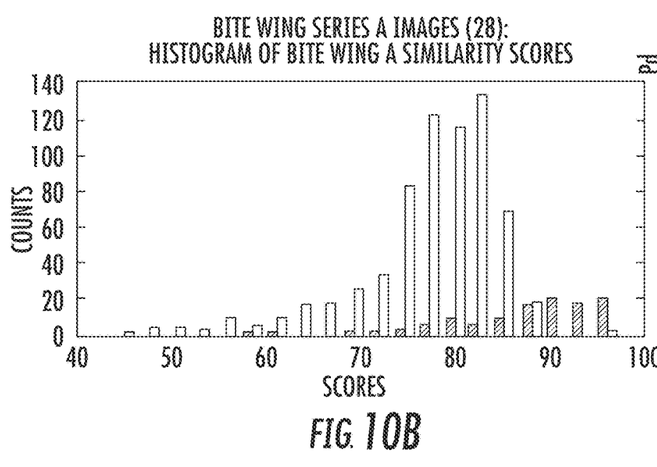
Figure 10C:
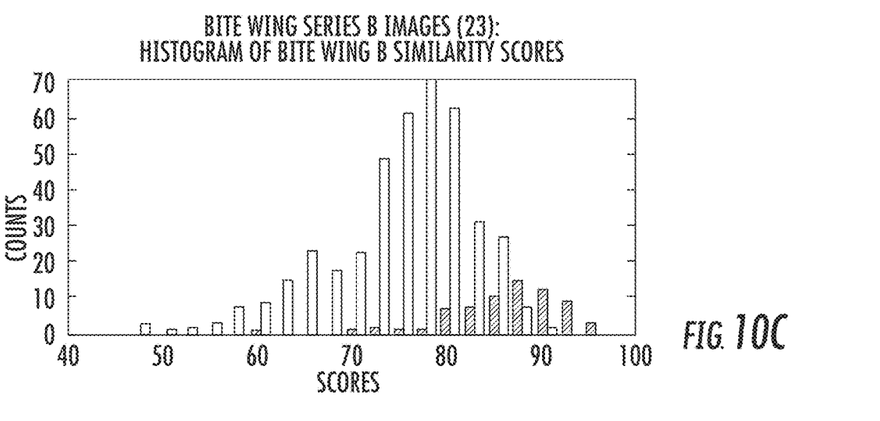
Figure 10D:
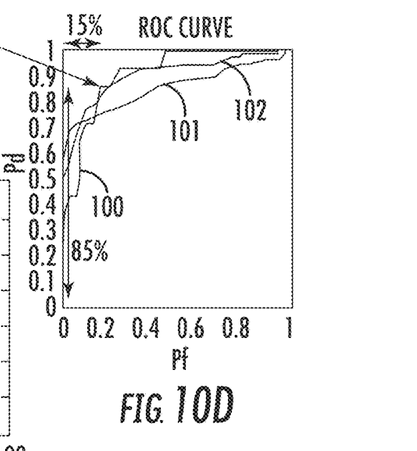
FIG. 10(d) is a diagram of associated ROC curves for the histograms of FIGS. 10(a)-10(c) for an example case study performed using the image processing approach of FIG. 8.

Referring additionally to the diagram 800 of FIG. 8, knowing the vertical direction in images simplifies the estimation of camera pose and camera motion, i.e., two fundamental image registration methods. This enables the alignment of different camera coordinate systems with measured vertical direction such that the y-axis of the camera is parallel to the vertical direction, and the x-z-plane of the camera is orthogonal to the vertical direction. In the illustrated example, a planar homography relationship between a perspective image and another image plane allows any point (X1) in one image plane to be mapped to any point (X2) in another image plane or view, as follows:

$$\vec{X}_2 = q_1\vec{b}_1 + q_2\vec{b}_2 + \vec{b}_0 = (\vec{b}_1, \vec{b}_2, \vec{b}_0)\begin{pmatrix}q_1\\q_2\\1\end{pmatrix} = B\vec{q}$$

where:

$B = (\vec{b}_1, \vec{b}_2, \vec{b}_0) \in \mathfrak{R}^{3\times 3}$ defines the plane $\vec{q} = (q_1, q_2, 1)^T$ defines the 2D coordinates of $\vec{X}_2$ with respect to the basis $(\vec{b}_1, \vec{b}_2)$ In a projective linear transformation (i.e., homography), the collineation between a world plane and its corresponding image plane is maintained even across perspective views of a plane in different images. To benefit from the presence of planes, these structures need to be detected. One approach to accomplish this is the use of line segment groups or image pyramids. Similar approaches have been used for ground plane homography detection. Of particular interest is the case where matching is difficult, e.g., when the baseline is wide or repeated patterns are present. Fundamental matrix estimation for uncalibrated image pairs is an important but sometimes difficult step in many vision applications. FIG. 9 presents an example of registration results for input static and moving input images 90, 91. An input image with warped region of interest (ROI) 92 is generated based upon the boundary points defined by the corners of the ROI trapezoid 93, which are used to define the disparity map 94. Homography is a good choice for registering dental imagery since it has minimal distortion or warping of pixels in an image. The 3D reconstruction results 95 are also shown.

With respect to the disparity map 94, alignment accuracy is calculated in terms of "red" and "green" pixels, from (total # pixels–# green–# red)/total # pixels. Red and green pixels correspond to changes in images, where a green pixel is greater than 200 and a red pixel is less than 200. Red pixels are values of at least 200 and green pixels are at most 200 from 8-bit pixel values.

2D radiographs do not provide depth details, and there is often a requirement for 3D data to achieve a better diagnosis by the radiologist. In some example embodiments, an approach for 3D reconstruction using uncalibrated radiographs may be provided for dentists to facilitate their evaluation of the degree of severity of teeth issues. 3D information retrieval from two radiographs may be achieved when the 3D position of the radiographs is known and when corresponding intensity matching points may be found in radiographs of the same scene.

A standardized average mouth distance serves as a reference for use in accurately determining depth data, especially when only two images are available, as with a bitewing X-rays. When considering a panoramic view, 3D reconstructed models are helpful. For panoramic X-rays, given the known scale of individual features and the ease with which those features can be distinguished, depth information becomes readily apparent.

Just as homography is a good for performing registration, change detection and 3D reconstruction, it is also good for matching dental radiographs. FIGS. 10(*a*)-(*d*) show results from a database with 9 patients and 61 images including panoramic and bitewing radiographs. Depending on requirements, one good similarity metric score is >80%, which is used as the baseline in this example. In the illustrated receiver operating characteristic (ROC) curves, panoramic data is represented by a curve 100, bite wing A data is represented by a curve 101, and bit wing B data is represented by a curve 102. If desired, visual verification of correct matches from automated process may also be performed. In the illustrated example, a similar point on the ROC curve 100 has approximately 85% of the H1 data to the right of 80 in the histogram of FIG. 10(*a*), and approximately 15% of the H0 data to the right of 80 in the histogram. A similarity metric score was determined as follows:

Alignment Accuracy=(total # pixels–# Image1# Image2)/total # pixels

Image1 and Image2 pixels correspond to changes in images

Image1 pixel>200 & Image2 pixel<200

Image2 pixel>200 & Image1 pixel<200

8 bit images

Many modifications and other embodiments will come to the mind of one skilled in the art having the benefit of the teachings presented in the foregoing descriptions and the associated drawings. Therefore, it is understood that the disclosure is not to be limited to the specific embodiments disclosed, and that modifications and embodiments are intended to be included within the scope of the appended claims.

That which is claimed is:

1. A dental imaging system comprising:
   an X-ray source;
   a first optical alignment device;
   a dental image collection device comprising
      a mouthpiece,
      at least one electronic X-ray sensor carried by the mouthpiece, and
      a second optical alignment device carried by the mouthpiece and cooperating with the first optical alignment device to facilitate optically aligning the mouthpiece with the X-ray source; and
   a dental image processing device coupled to the at least one electronic X-ray sensor and configured to generate a disparity map image using parallax from overlapping viewpoints of a given area from dental images collected at different times.

2. The system of claim 1 wherein the first optical alignment device comprises an optical target; and wherein the second optical alignment device comprises at least one optical source.

3. The system of claim 1 wherein the first optical alignment device comprises at least one optical detector; and wherein the second optical alignment device comprises at least one optical source.

4. The system of claim 1 wherein the first optical alignment device is carried by the X-ray source.

5. The system of claim 1 wherein the second optical alignment device comprises a plurality of laser light sources.

6. The system of claim 1 wherein the at least one X-ray sensor comprises a plurality of integrated circuit (IC) sensors.

7. The system of claim 1 wherein the dental image processing device is configured to process dental images using a homography algorithm prior to generating the disparity image.

8. The system of claim 1 wherein the dental image processing device is configured to process dental images using a homography algorithm prior to generating the disparity map image.

9. The system of claim 1 further comprising at least one actuator coupled to the X-ray source; and wherein the dental image processing device is configured to operate the at least one actuator based upon the first and second optical alignment devices.

10. A method for collecting dental imagery, the method comprising:
    inserting a dental image collection device in a patient's mouth comprising a mouthpiece, at least one electronic X-ray sensor carried by the mouthpiece, and a second optical alignment device carried by the mouthpiece, the dental image collection device being coupled to a dental image processing device;
    aligning an X-ray source with the mouthpiece by optically aligning a first optical alignment device and the second optical alignment device; and
    using the X-ray source and a dental image processing device to collect X-ray data from the electronic X-ray sensor to generate a disparity map image using parallax from overlapping viewpoints of a given area from dental images collected at different times.

11. The method of claim 9 wherein the first optical alignment device comprises an optical target; and wherein the second optical alignment device comprises at least one optical source.

12. The method of claim 9 wherein the first optical alignment device comprises at least one optical detector; and wherein the second optical alignment device comprises at least one optical source.

13. The method of claim 9 wherein the first optical alignment device is carried by the X-ray source.

14. The method of claim 9 further comprising processing the dental images using a homography algorithm with the dental image processing device prior to generating the disparity map image.

\* \* \* \* \*